(12) United States Patent
Quistgaard et al.

(10) Patent No.: US 7,532,201 B2
(45) Date of Patent: May 12, 2009

(54) POSITION TRACKING DEVICE (75) Inventors: Jens U. Quistgaard, Seattle, WA (US); Charles S. Desilets, Edmonds, WA (US); Tim Etchells, Bothell, WA (US); Gregory Paul Darlington, Snohomoish, WA (US)

(73) Assignee: LipoSonix, Inc., Bothell, WA (US)

( * ) Notice: Subject to any disclaimer, the term of this patent is extended or adjusted under 35 U.S.C. 154(b) by 716 days.

(21) Appl. No.: 11/027,911

(22) Filed: Dec. 29, 2004

(65) Prior Publication Data

US 2005/0187463 A1    Aug. 25, 2005

Related U.S. Application Data

(60) Provisional application No. 60/533,528, filed on Dec. 30, 2003.

(51) Int. Cl.
*G09G 5/08* (2006.01)

(52) U.S. Cl. .................................. 345/166; 606/130

(58) Field of Classification Search ................. 345/163, 345/166; 600/427, 447, 459; 606/130
See application file for complete search history.

(56) References Cited

U.S. PATENT DOCUMENTS

| | | | |
|---|---|---|---|
| 4,137,777 A | 2/1979 | Haverl et al. | |
| 5,404,387 A | 4/1995 | Hammond et al. | |
| 5,810,008 A * | 9/1998 | Dekel et al. | 600/443 |
| 6,554,771 B1 * | 4/2003 | Buil et al. | 600/459 |
| 6,618,038 B1 | 9/2003 | Bohn | |
| 7,244,234 B2 * | 7/2007 | Ridley et al. | 600/459 |

* cited by examiner

*Primary Examiner*—Richard Hjerpe
*Assistant Examiner*—Tom V Sheng
(74) *Attorney, Agent, or Firm*—Townsend and Townsend and Crew LLP (57) ABSTRACT

A position tracking device is disclosed combining one or more optical sensors in a housing with a medical device. The medical device may be an insertion device or one that produces radiant energy. The device may utilize an on-board processor or an external processor to track position data generated by the optical sensors and correlate the treatment regime of the medical device. Alternative embodiments and methods of use are also described.

20 Claims, 9 Drawing Sheets

POSITION TRACKING DEVICE

CROSS-REFERENCES TO RELATED APPLICATIONS

This application claims the benefit of prior provisional application No. 60/533,528, filed on Dec. 30, 2003, the full disclosure of which is incorporated herein by reference.

The subject matter of the present application is related to that of the following applications: Ser. No. 10/750,370, entitled "Medical Device Inline Degasser", Ser. No. 10/751,344, entitled "Articulating Arm for Medical Procedures", Ser. No. 10/750,369, entitled "Disposable Transducer Seal", 60/533,988, entitled "Method for Planning and Performing Ultrasound Therapy"; 60/534,036, entitled "Ultrasound Therapy with Hood Movement Control"; 60/533,958, entitled "Systems and Methods for the Destruction of Adipose Tissue"; 60/534,034, entitled "Component Ultrasound Transducer"; the full disclosure of each of these applications are incorporated herein by reference.

BACKGROUND OF THE INVENTION

1. Field of the Invention

The present invention relates to a motion tracking device for use on human skin, and adapted to plot the location of a medical device on a computer monitor, or a topographical map of human tissue.

2. Description of the Prior Art

Presently a large number of medical procedures are done by hand relying solely on the experience and expertise of a physician. Procedures occur every day from the drawing of blood, to the insertion of catheters, or from diagnostic ultrasound scans for imaging a patient, to therapeutic procedures to destroy unwanted tissue. All of these historically rely on the experience and judgment of the physician based on tissue and organs the physician cannot see, but can generally gauge the general position of those tissues.

Few technologies exist at present for a physician to accurately map the surface area of a patient's epidermis, or correlate the surface map with a detailed three dimensional map of the tissue beneath the skin. Further complicating the matter is the need for the physician to have access to the skin or surface area the physician may wish to produce a map of. The necessity of being able to perform a medical procedure at a particular location precludes the utility of a device that accurately measures either surface movement and features, but makes imaging below the surface virtually impossible.

U.S. Pat. No. 4,137,777 to Haverl et al., provides for an apparatus for dynamic focusing and multiple plane scaling of ultrasound to provide repeatability of scan results by removing some level of operator placement of the transducer. However this apparatus does not correlate the image data with a surface map of the patient's skin. Primarily because the apparatus is designed to image organ tissue within the body cavity, and subject to internal movement.

U.S. Pat. No. 5,404,387 to Hammond et al., provides for a system and method for scanning the human body using X-radiation. The device being designed primarily to scan for foreign objects on or in a person. The device converts X-radiation into a video image for display. However this invention does not deal with tracking a medical device on a person nor assist a physician in carrying out a medical procedure. Position tracking on a patient's skin is not provided for here either.

However, position tracking devices are well known in the field of computer science. Nearly every personal computer utilizes some form of "mouse" for position tracking of a cursor on a display screen. The development of computer mouse technology has seen an explosion of different tracking devices. Mechanical mice use a roller-ball mounted within a cell and having multiple roller axes that roll counter to the direction of the track ball in the way of a toothless gear. The mechanism calculates the motion of a track ball and converts that motion into a direction and speed indicator on a screen. The visual display shows a cursor, in the form of an arrow, I-beam or other icon.

Optical mice work by image correlation based on the surface they are tracking over. Early optical mice required light reflecting grids or other special surfaces in order for them to accurately track direction and speed of movement. More recent computer mice allow for digitizing an image of the surface they are moving over and comparing sequential images to determine the change in position. The change in position information is usually processed by an on-board microprocessor that provides a computer with both speed and direction information.

For example, the optical tracking elements of an optical mouse include a small light emitting diode (LED) and a detector functioning as a small camera capable of taking a high number of pictures every second. Camera operations can be performed by a complimentary metal-oxide semiconductor (CMOS) and sends each image to a digital signal processor (DSP). The DSP can be on board or in a separate computer. The DSP can compare sequential images based on an internal clock, or using the DSP's internal clock and compare how images have moved from one frame to the next. This allows the DSP to determine both direction and speed of movement of an optical mouse. There are numerous ways optical mice are constructed and designed to provide pointer/cursor information for a user on a computer screen, the above description is merely illustrative of a generic computer mouse.

A feature optical and mechanical mice share is the ability to track frame to frame or roller movement to roller movement. In essence, the relative location of the mouse is not important so long as the device can track over the surface it is moving on. In this manner a user is able to pick up a mouse when it runs off the edge of a mouse pad, or the user runs out of room, and then replace the mouse on the surface and resume tracking the cursor on the monitor. The cursor on the monitor does not move during the replacing of the mouse, so the cursor position is never lost on the screen.

U.S. Pat. No. 6,618,038 to Bohn, provides for a computer pointing device having two optical encoders, allowing the computer mouse to track both position and orientation changes on a video monitor. However the pointing device is designed for use with a computer system to serve as a pointing device, and not as a position tracking device.

The use of optical sensors and mechanical sensors as pointing devices does not address the issue of an accurate position tracking device. The distinction is made in that the pointing device tracks the position of a cursor in a virtual environment, while a position tracking device tracks a physical position on a surface without concern for any virtual positioning or location. Thus while computer mice can be adjusted for slow or fast tracking over a surface set to a users preference, a position tracking device must be a true representation of actual speed and movement over a surface. The use of a position tracking device can be of great assistance in the medical arts.

Thus there remains a need in the field of medical procedures for a precise position tracking device utilizing reliable sensor technology.

There is further a need for a position tracking device that can be used in tandem with a medical device.

There is still further a need for a position tracking device that can accurately position radiant therapy treatments in a three dimensional environment.

There is still further a need for a position tracking device that can operate in conjunction with a medical device controller or a therapy procedure program to coordinate effective dosing in a two or three dimensional environment without relying on discretionary input from a user.

BRIEF SUMMARY OF THE INVENTION

Thus one objective of the present invention is to provide for a precise position tracking device for medical applications using reliable sensor technology.

Another objective of the present invention it to provide for a position tracking device that can be used in combination with one or more medical devices.

Yet another objective of the present invention is to provide for a position tracking device that can accurately position a radiant therapy device in a three dimensional environment.

It is still further an objective of the present invention to provide for a position tracking device that can operate in conjunction with a medical device controller or a therapy procedure program to coordinate dosing in a two or three dimensional environment without relying on a physician for dosing.

At least some of the objectives are realized utilizing a position tracking device for recording movement of a medical device over a patient. The position tracking device has a housing adapted to be moved relative to a patient. The housing has a top section and a bottom section. The bottom section has a primary transmissible window, and at least one secondary transmissible window. There is also a means for sensing movement through the secondary transmissible window(s). An asymmetric flange is attached to the bottom section. The flange is positioned substantially near the patient when the housing is moved relative to the patient. There is at least one medical device positioned within the housing to transmit energy through the primary transmissible window.

In another embodiment there is a position tracking device for recording movement of a medical device over a patient. The position tracking device has a housing adapted to be moved relative to a patient. This housing having a top section and a bottom section, where the bottom section has at least one transmissible window. The housing has an aperture for slidably receiving a medical device. The aperture extends there through from the top section to the bottom section. There is a means for sensing movement through the transmissible window and an asymmetric flange attached to the bottom section. The flange is positioned substantially near the patient when the housing is moved relative to the patient.

In yet another embodiment, the position tracking device comprises a housing adapted to be moved relative to a patient. The housing has a top section and a bottom section. The bottom section has a primary transmissible window, at least one secondary transmissible window and an aperture for slidably receiving a medical instrument. There is also a means for sensing movement through the secondary transmissible window(s). An asymmetric patterned flange is attached to the bottom section wherein the flange is positioned substantially near the patient when the housing is moved relative to the patient. A medical imaging device is positioned within the housing to image patient tissue through the primary transmissible window.

There is also a method of position tracking over human tissue, the method having the steps of placing a position tracking device on a patient then defining a reference position. Once the reference position is defined, the step of calibrating the position tracking device to the reference position is done. The next step is treating the patient with a medical device enclosed within the position tracking device while tracking and recording all movement data.

Variations and equivalents within the spirit of the invention are described below.

DETAILED DESCRIPTION OF THE INVENTION

In the present disclosure it will be useful to understand that the "origin" referred to below has to deal with the placement of the position tracking device at the outset of a medical procedure. When the position tracking device is first placed on to a patient, there is a method provided below of establishing the starting position of the device and making sure that position is readily identifiable through out the procedure in case the starting placement of the device is needed. We refer to the starting placement of the device as the "reference position" and/or the "origin."

Within the device there is a medical device or affecter for transmitting energy into the patient. The focal point of the energy transmission occurs through a transmissible window. The center of the energy transmission area, within the area of the transmissible window, is the "affecter center." When the device is in operation, the optical sensors are used to determine the movement and orientation of the device about the affecter center. Usually the affecter center is derived mathematically since an optical sensor cannot be positioned in the exact same location in the housing as the affecter center. When the medical device is an insertion device, then the affecter center is the point on the patient, through which the insertion device is going to penetrate the patient's skin.

The present invention relates to a position tracking device for recording movement of a medical device over a patient. The position tracking device has a housing adapted to be moved relative to a patient. The housing has a top section and a bottom section. The bottom section has a primary transmissible window, and at least one secondary transmissible window. There is also a means for sensing movement through the secondary transmissible window(s). An asymmetric flange is fixedly attached to the bottom section. The flange is positioned substantially near the patient when the housing is moved relative to the patient. There is at least one medical device positioned within the housing to transmit energy through the primary transmissible window.

In a first embodiment, the housing has a cylindrical form. The top section comprises a grip for a user to manipulate the device. The bottom section contains a medical device and a means for sensing the movement of the device over a patient. The bottom surface is preferably smooth and has a low coefficient of friction to facilitate an easy glide over the patient's skin. The bottom section also has a plurality of transmissible windows.

The primary transmissible window is a portal through which radiant energy of the medical device can affect the patient. The transmissible window is preferably solid, yet transparent to the energy emission of the medical device. The primary transmissible window is preferably made of a smooth material, so as to reduce drag and friction as the device moves over the patient.

The secondary transmissible windows allow optical sensors to image the patient's skin. Using well known principles established in the art of computer pointing devices, optical "mice" technology can be adapted for medical purposes. The optical sensors image and record data in the same manner as computer pointing devices. However the signal processing done with the image data is different.

Image data from the optical sensors is communicated to a processor operationally associated with the optical sensors. If a single optical sensor is used, the processor determines the movement and orientation changes from the data provided by the single optical sensor. In this case the medical device or affecter center is offset by some distance $\Delta$ from the optical sensor. The processor determines movement and orientation changes from the true position of the optical sensor, or calculates movement and orientation changes from an artificial position of the distance $\Delta$ from the optical sensor to the affecter center. Preferably two or more optical sensors are used to generate image data and relay the data to the processor. Using multiple optical sensors it is possible to correlate the image data from all the optical sensors. This allows the determination of movement of the affecter center with much greater accuracy and precision than with a single optical sensor.

The result of the processor calculation is position data that includes the movement position of the device from one image frame to the next. The data may also include changes in orientation in the event the device is rotated about an axis perpendicular to the plane of the patient and device contact. An operator may move the device during the course of a medical procedure in many different ways, and all movement, whether linear, rotational or angular is determined and recorded. The recording of the data may be done internally such as on a memory device, or relayed to an external device such as a computer, or medical device controller. The processor retains sufficient memory of the treatment area extending from the origin that it can identify when the device retraces a path or area that the device has previously passed over. Signals to this effect are relayed to the computer, medical device controller, or to a indicator on the housing itself.

Positioning the device requires the ability to reliably place the device on the same position or origin each time the need arises. For instance, in a therapeutic ultrasound procedure it is desirable to track tissue volumes that have been treated and to distinguish them from tissue that has not been treated. Defining a reference position or origin before a procedure begins allows the device to be repositioned in the same place on the patient at any time. The device has an asymmetric flange about the bottom section. When the device is placed in contact with the patient, the asymmetric flange rests on the patient's skin. A physician can trace the asymmetric flange using a medical grade ink or a body marker. In the device loses contact with a patient during a medical procedure, the physician can replace the device back on the origin so the outline of the flange is aligned with the flange itself.

Alternatively the flange may be molded into the housing, or made into an attachable accessory. The flange may be replaced by an electronic sensor that allows the position tracking device to be repositioned on the origin (an electronic flange equivalent). Various equivalents are apparent so long as there is a reliable method to returning the device to the origin and in the proper orientation.

A medical device is incorporated into the housing. The medical device can transmit energy through the primary transmissible window. The medical device may be a therapeutic device, a diagnostic instrument, imaging device or other sensor. There are numerous possibilities. It will be apparent to those skilled in the art that the primary transmissible window must be substantially transparent to the energy produced by the medical device. Thus if the medical device is a laser, the transmissible window should be optically transparent to the frequency of light corresponding to the laser. If the device is an ultrasound device the transmissible window must be acoustically transparent, though it may be opaque to light. Similarly if the medical device is a microwave emitter the transmissible window must not interfere with the transmission of microwave energy. A radiation seed may also be used as the medical device, for instance for the treatment of skin cancer. In this case the housing of the device must contain sufficient shielding to protect the physician and the patient, while the transmissible window is preferably an actuated window so that it can be opened or closed to allow radiation to pass to the patient only when desired.

In a second embodiment, the position tracking device has a housing having at least one transmissible window, and an aperture through the housing for slidably receiving a medical instrument. In this embodiment the housing has one or more transmissible windows used for the optical sensors as described above. However the medical device is not incorporated into the housing. Instead there is an aperture for slidably receiving a medical instrument, such as a syringe, biopsy needle, catheter insertion tool or the like. The aperture is adapted to receive medical instrument to be inserted into the patient.

In a third embodiment the position tracking device has a housing having a primary transmissible window and at least one secondary transmissible window. The primary transmissible window allows an imaging sensor to scan or image the patient's tissue while the optical sensor(s) track the movement and position of the device through the secondary transmissible window(s). When the device is in the proper location a medical instrument may be inserted into the patient through the aperture. The medical imaging sensor combined with the optical sensors provide for a greater degree of accuracy in the placement of an insertion device than previously possible in a single device.

Figure 1A:
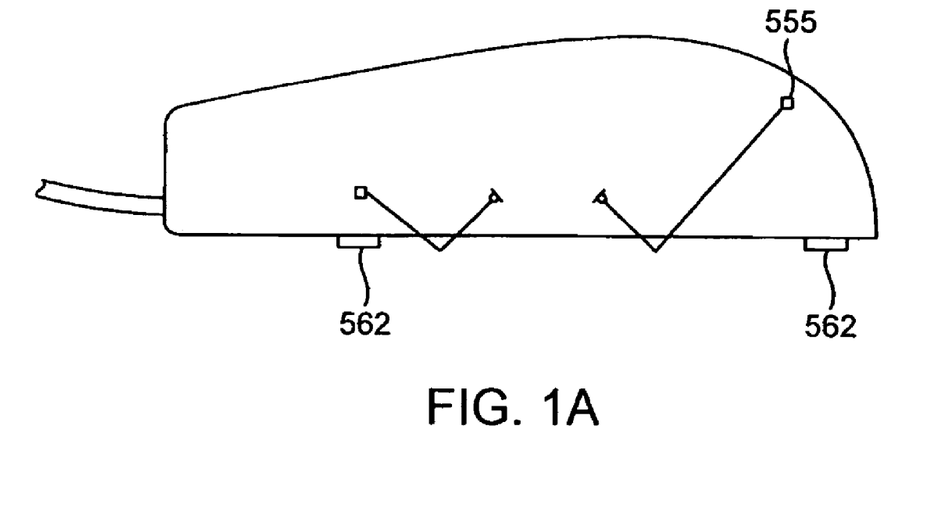
FIG. 1A is an illustration of a prior art computer mouse.
Figure 1B:
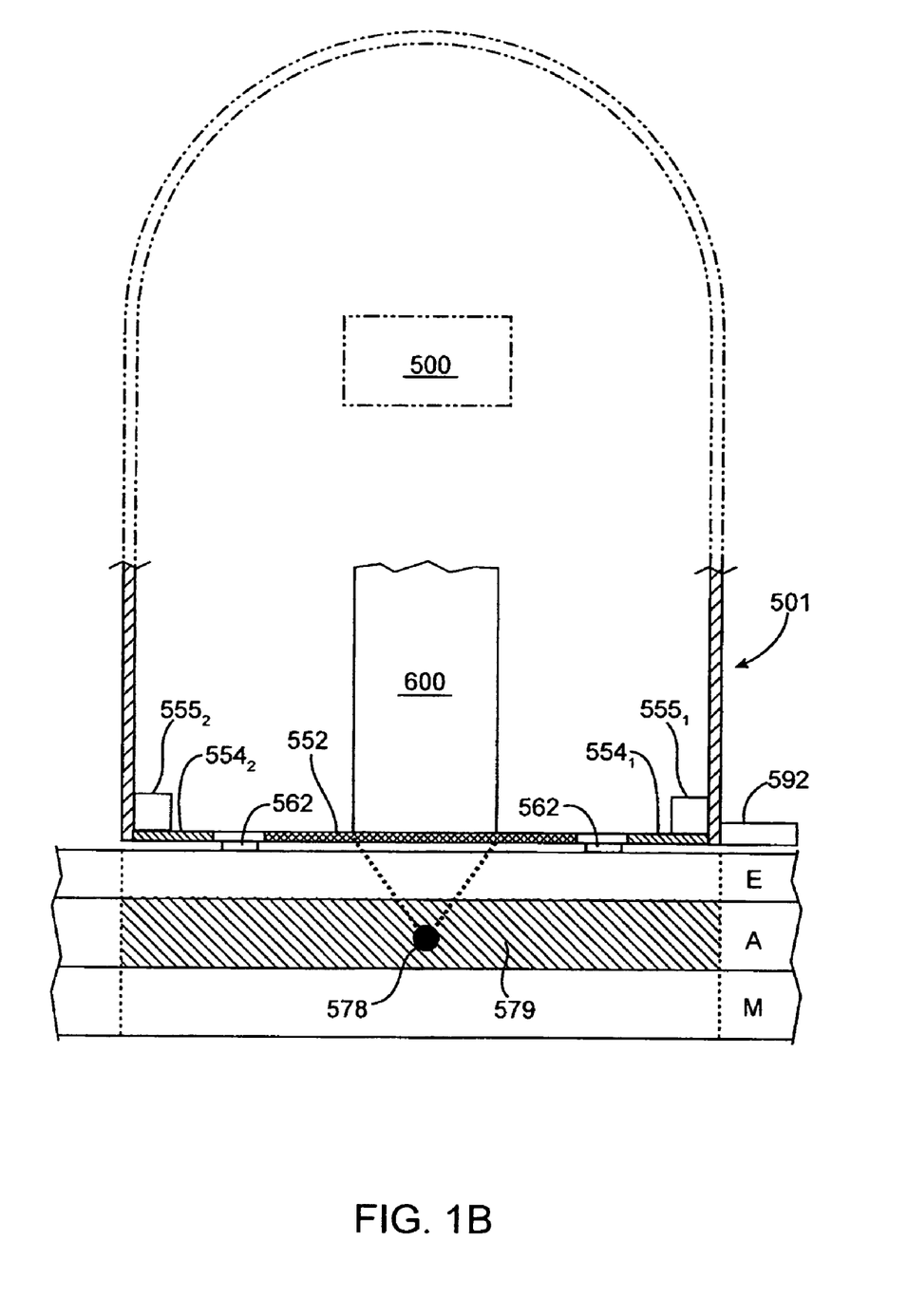
FIG. 1B is an illustration of the present invention in operation.

Turning now to the drawings, FIG. 1A illustrates an optical mice of the prior art Having a pair of optical sensors used for tracking changes in orientation. The mouse utilizes two optical detectors $555_1$, $555_2$ so a user can see on a computer screen the changes in orientation as he or she moves the computer pointing device. FIG. 1B illustrates a position tracking device of the present invention and a depth model of tissue as the device is moving over human tissue. There is a housing 500 riding over a patient P wherein the optical sensors $555x$-$n$ are tracking across the surface of the patients skin. One or more slides or skids 562 are on the lower section 501 of the housing 500 to facilitate gliding of the housing over the skin. A medical device 600 is enclosed within the housing 500 and has an affecter center 578 artificially defined under the medical device. There is a first transmissible window 552 and a plurality of secondary transmissible windows 554x-n for the medical device 600 and a plurality of optical sensors $555_{x1-xn}$. The position tracking device generates a three dimensional map of treatment based on either the mapping of the internal tissue, or the mapping of the affecter radiant energy in the affecter zone 579, or an overlay of both. The housing may have one or more actuators 582, 584, 586 positioned on the top section 564 for easy reach by a user. There is a grip 568 on the housing to assist a user in manipulating the housing. The bottom section 566 incorporates an asymmetric flange 592 used to calibrate the positioning of the housing. Optionally the housing may incorporate a visual indicators, such as a display panel 242, a data or communication cable 572, and/or an on-board processor 570. In addition the housing may be attached to additional devices as described below.

Figure 1C:
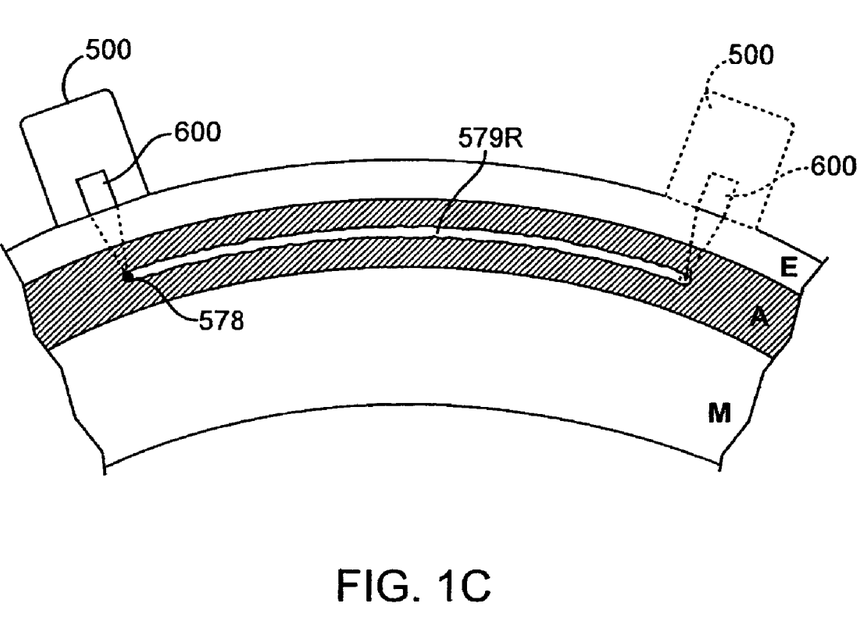
FIG. 1C shows a volume map of a patient created using an ultrasound device.

FIG. 1C illustrates a three dimensional map. Using the position tracking device in combination with an imaging ultrasound device, a reliable and highly accurate three dimensional map of patient tissue can be created. Unlike three dimensional images from prior art ultrasound devices, the coordination of the precise movement of the position tracking device over the patient combined with detailed ultrasound image data can be used to create a tissue map. A computer can track the precise position of the device over the patient and correlate the ultrasound image data to the position. As the housing 500 moves over the patient body each new image from the ultrasound image device is correlated to its respective two dimensional shift on the surface skin. Image distortions due to changes in radius of scan, and distortions based on the normal limitations of ultrasound imaging can be corrected by using an image averaging or image compensation protocol. The ultrasound transducer becomes the medical device 600 in this case. The volume of tissue that can be scanned in one pass of the therapy head 500 over the patient body P is the scan line 579R.

Figure 2A:
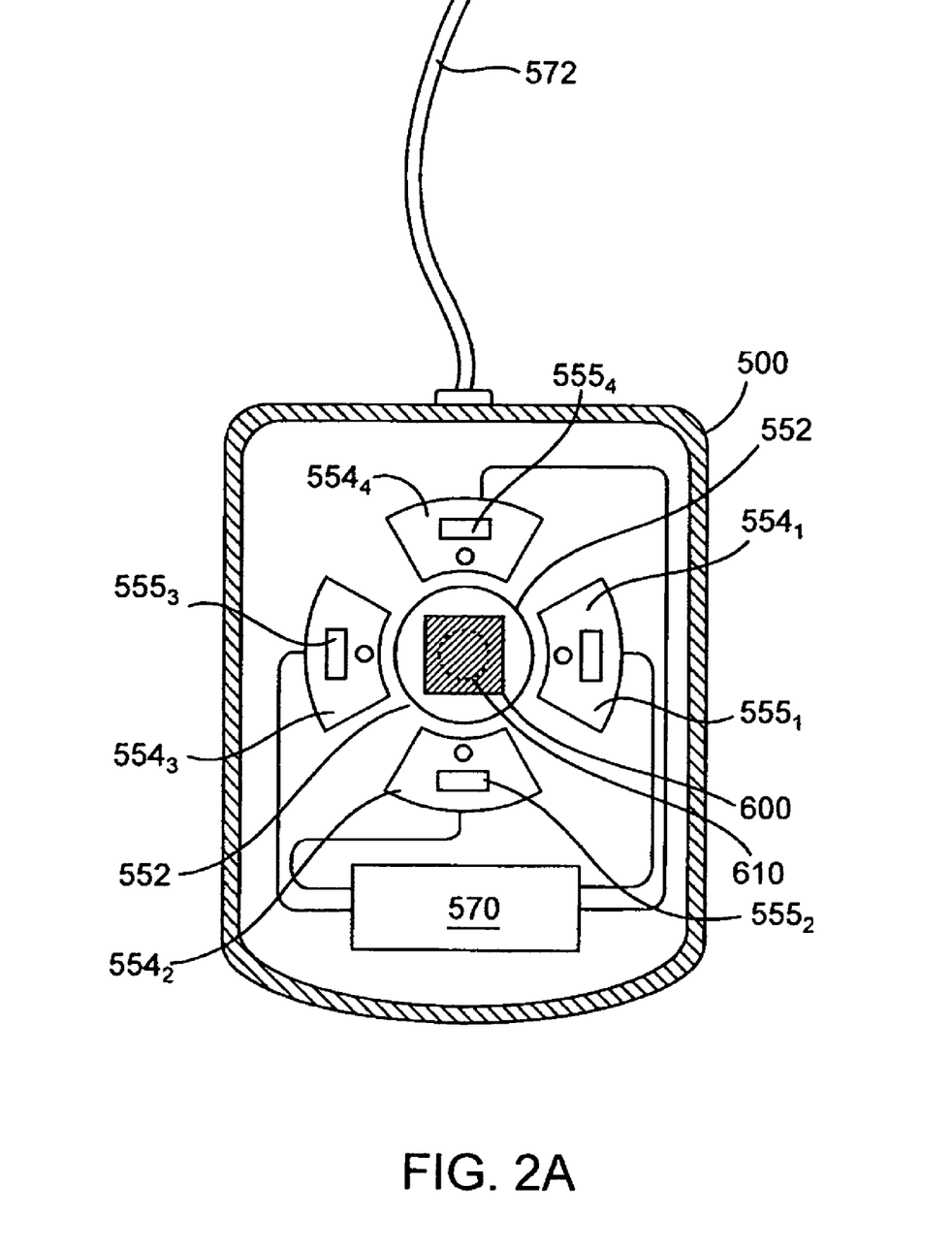
FIG. 2A is a schematic of the present invention.

FIG. 2A illustrates a cut away view of the device looking up through the bottom section. The housing 500 provides the structural basis for the other components. There is a medical device 600 able to transmit radiant energy through the primary transmissible window 552. Surrounding the medical device 600 is a plurality of optical sensors $555_{x1-4}$. Each optical sensor can image the patient through a plurality of corresponding secondary transmissible windows $554_{x1-4}$. The optical sensors are linked to an on board processor 570. The processor 570 receives data from each optical sensor and averages the data to determine the centered position 610 of the medical device 600. Data generated by the optical sensors $555_{x1-4}$ or the processor 570 can be relayed to an external computer 400 through a communication link 572. The communication link 572 may be wireless if so desired.

Preferably the processor has sufficient memory attached to it that it can retain a library of the path the device has traveled during a procedure. Using a warning light or display panel 242, the device can alert a user if the treatment path is about to be retraced by the device. The warning allows a user to prevent retreating the same area. If the processor 570 is in communication with a computer 400, or a therapy controller 250, then when the device retraces steps, the processor can alert the computer 400, or therapy controller 250 so as to prevent the medical device 600 from radiating energy into the same tissue.

The device also has an asymmetric flange 592 about the bottom section 501 to facilitate replacing the device into the reference position. The asymmetric flange 592 is used to trace out the footprint of the device on to the patient so that the starting location of the device is always known. As the device is moved over the patient, the optical sensors provide continuing tracking data to the processor. The data is recorded on board in a memory device, or relayed to the external computer for storage and data analysis. The position data is can be used by the medical device controller to determine what volumes of tissue have been treated by the medical device affecter and what volumes have not been treated. Should the device pass over an area of the patient that has been previously exposed to radiate energy, the onboard computer may disable the medical instrument so as to not endanger anyone.

Figure 2B:
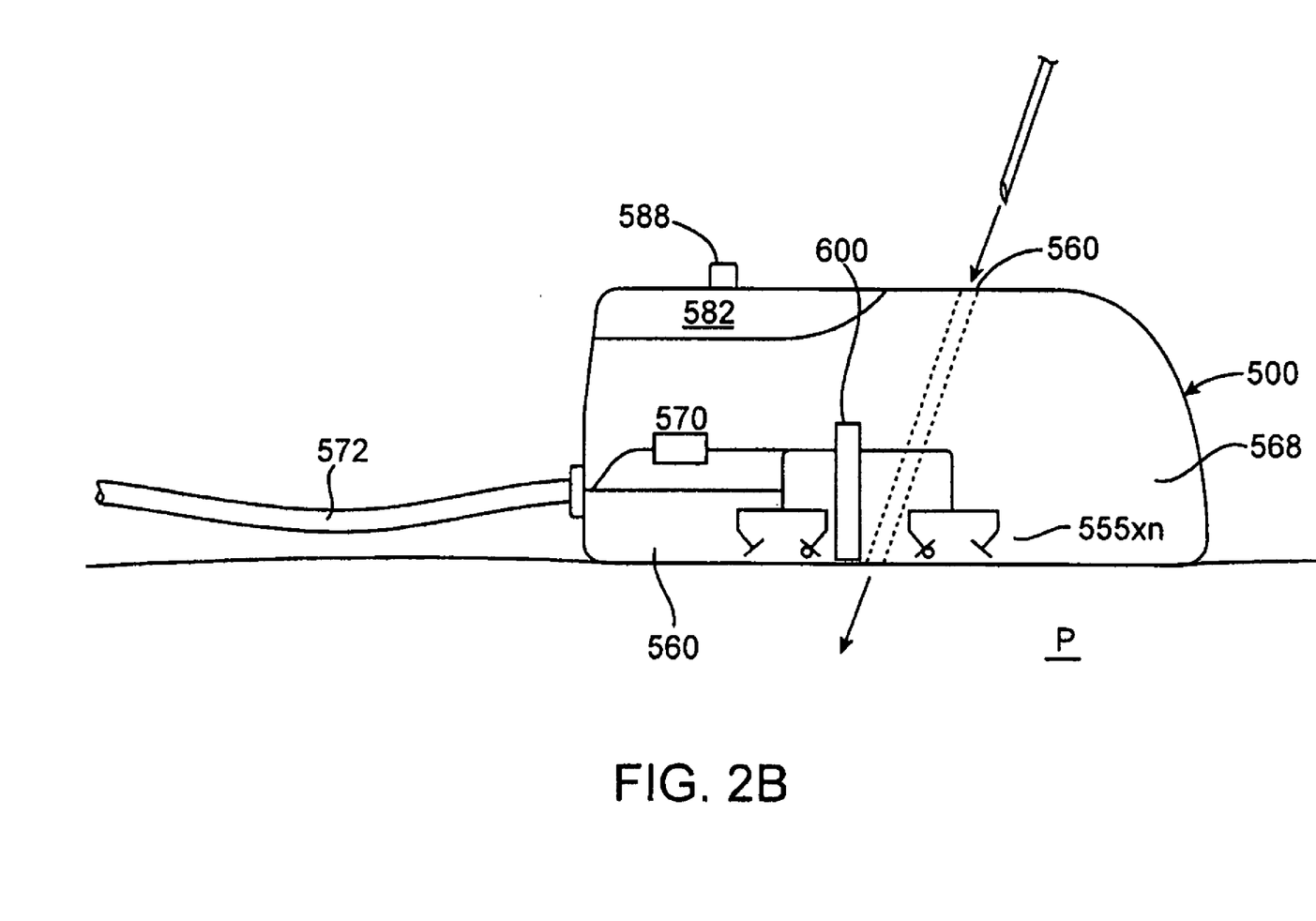
FIG. 2B represents an alternate embodiment having an aperture.

FIG. 2B provides a side view of an alternative embodiment. The housing 500 is shown once again in a cut away view with the optical sensors $555_{x1-xn}$ positioned to view the patient through a plurality of secondary transmissible windows $554_{x1-xn}$. There is a first medical device 600 in the form of an A-line ultrasound transducer and a second medical instrument 558 in the form of a needle. The top section 564 has a grip 568 for a physician to firmly grasp the device and maneuver it as necessary. Once the physician has placed the device in the proper position, the physician may insert a needle or other intrusive device through the aperture 560.

The affecter center 578 is an artificial point established where the aperture 560 opens to the bottom section 501. This is the insertion point at which the medical instrument 558 will enter the body of the patient.

In a procedure where the physician seeks to insert a device into the patient it is uncertain whether a reference position must be established. If there is no need to establish a reference position or origin, then the flange 592 may be omitted. However if the path taken by the device is of concern to the physician, the device can record the image data from the optical sensors to generate a library of position that have been scanned by the device, and regions that have not been scanned within the treatment area.

Figure 2C:
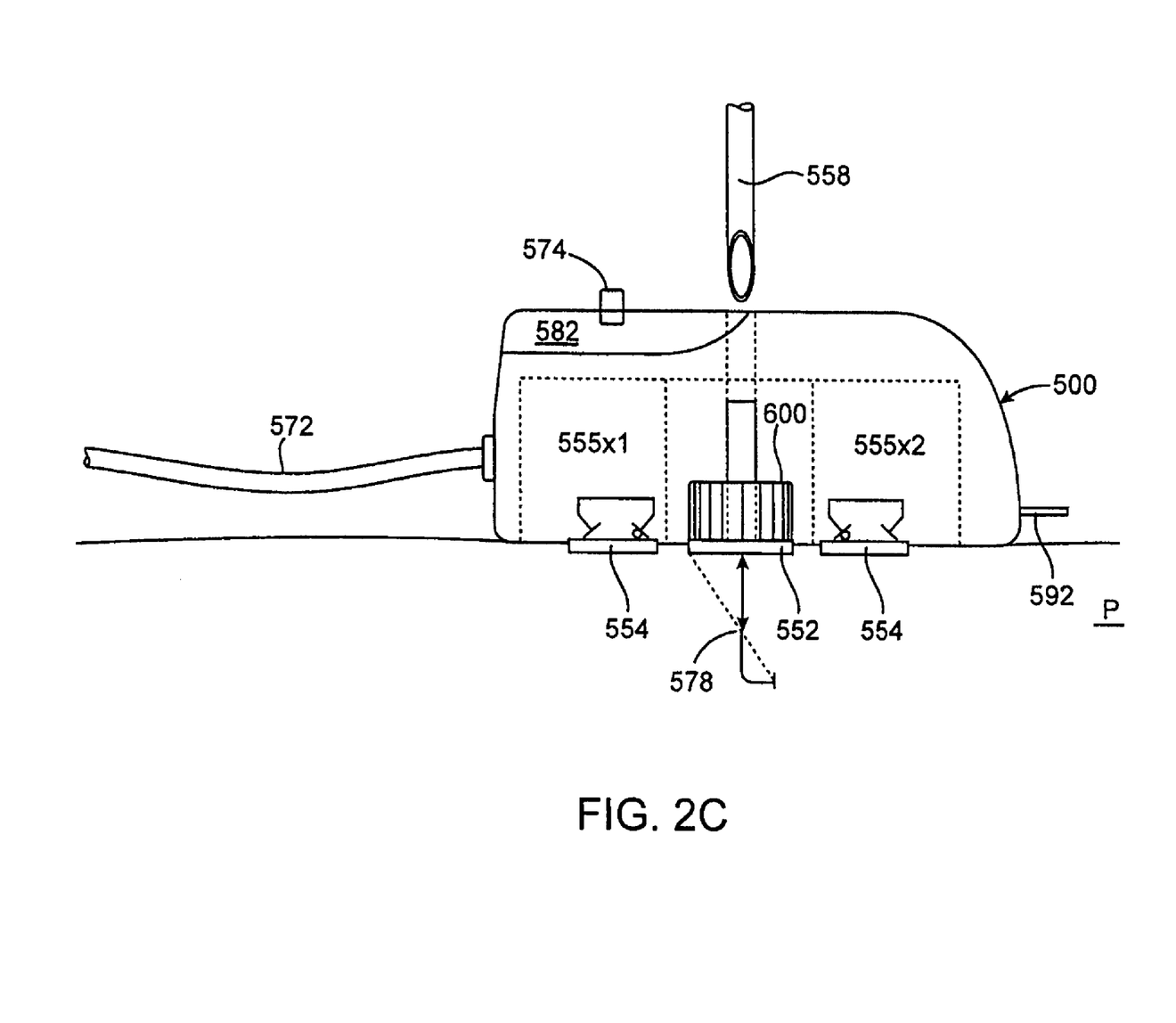
FIG. 2C illustrates an alternate embodiment having a variable position aperture.

FIG. 2C shows an embodiment similar to that in FIG. 2B. The housing 500 Contains a plurality of optical sensors $555_{x1-xn}$. There is a first medical device 600 is an imaging ultrasound transducer able to produce a scan of a tissue region. The affecter center 578 is centered in the middle of the imaging transducer. An aperture 560 extends from the top section 564 through the bottom section 566 and through the first medical device 600, an imaging transducer in this case. The affecter center 578 is fixed within the diagnostic ultrasound image field. An insertion device 558 is passed through the aperture 560 and enters the patient at the affecter center.

By using the position tracking device illustrated here, a physician can move the device over the surface of the patient while collecting detailed three dimensional tissue data. The ultrasound imaging device produces detailed information of the tissue beneath the surface while the optical sensors provide for precise information as to the location of the ultrasound scans. The image data and the optical sensor information can be combined by relaying the information to a computer 400 through the communication link 572. The information can be correlated producing an highly accurate three dimensional map of the patient tissue. This map allows for the precise placement of the insertion device 558. While the drawing shows the aperture 560 oriented in a perpendicular alignment with the bottom section 501, the aperture may be angled as shown in FIG. 2B. Optionally the aperture may be changed within the housing 500 by using a pivot sling, turret device or other means to change the angle of approach of the insertion device 558 to the patient P.

Figure 3A:
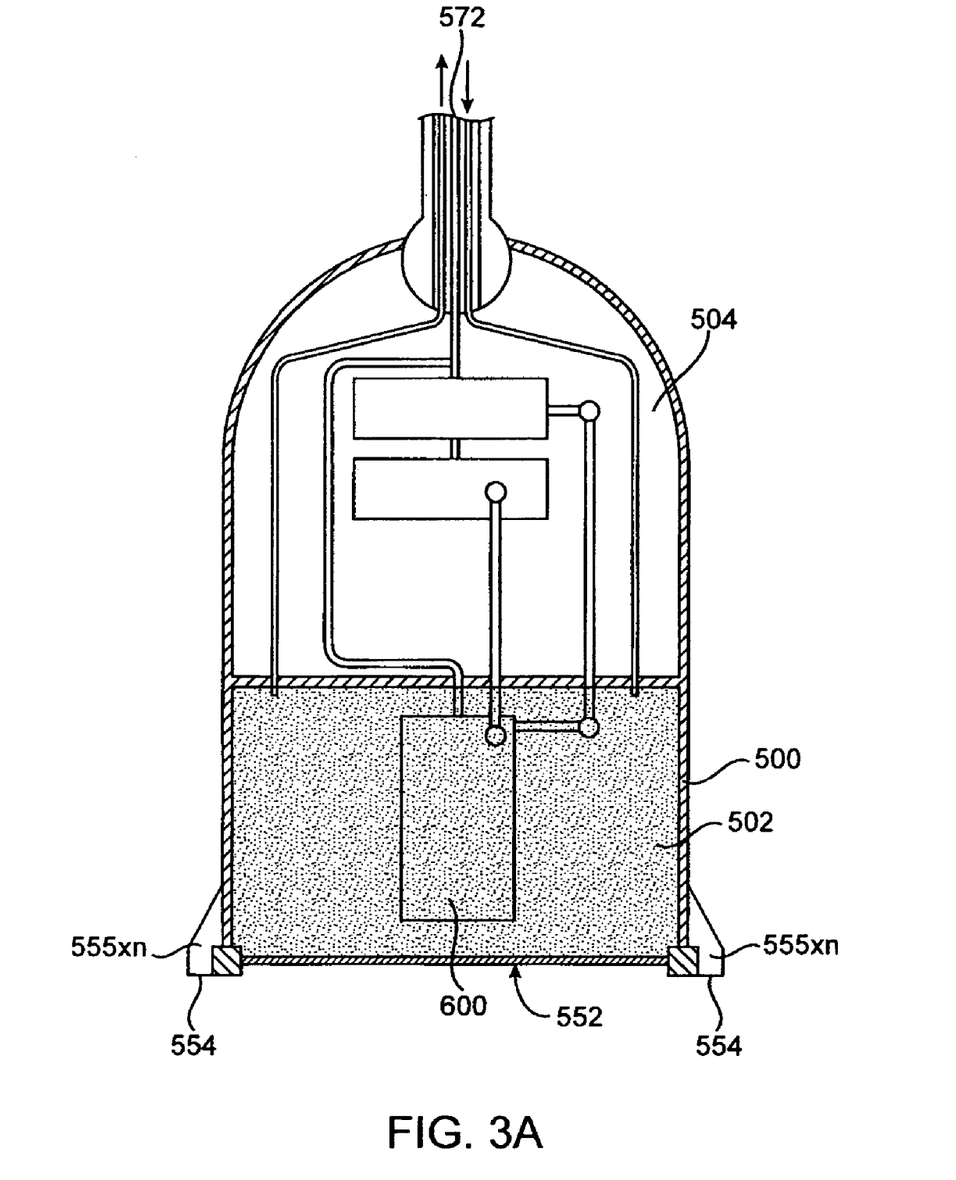
FIG. 3A illustrates a cylindrical housing used with multiple medical devices.

FIG. 3A illustrates an alternative embodiment where the housing 500 is more cylindrical in shape. The upper chamber 504 contains additional electronic and mechanical instruments needed for the proper operation of the first medical device 600. If the position tracking device is to operate independently without attachment to a computer or other peripheral device, then the top section also contains a power supply (not shown). The lower chamber 502 contains the first medical device 600. There is a primary transmissible window 552 being essentially transparent to the radiant energy the first medical device 600 produces. The optical sensors $555_{x1-xn}$ are arranged around the perimeter of the bottom section 566 of the housing 500. The position of the optical sensors $555_{x1-xn}$ around the perimeter can serve the same function as an asymmetric flange. Each optical sensor $555_{x1-xn}$ has a corresponding secondary transmissible window $554_{x1-xn}$. It should be noted that if the primary transmissible window can be made from a material that is also transparent for the optical sensors, then a single transmissible window can be used for the first medical device 600 and the optical sensors $555_{x1-xn}$.

Figure 3B:
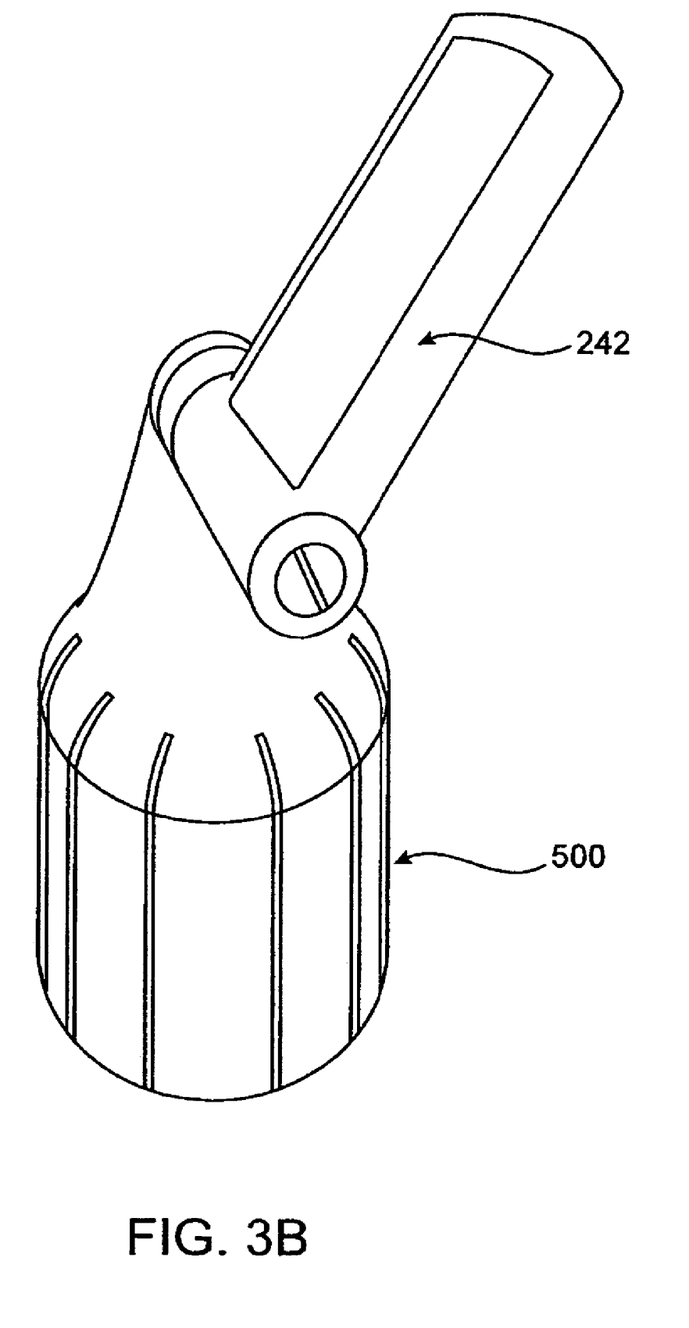
FIG. 3B provides an external view of the cylindrical housing.

FIG. 3B illustrates the position tracking device 550 having an attached display 590. The display allows a physician to visualize the progress of the device from the reference position or origin using a map showing the location of the origin and the current position of the device. Although illustrated here with a display, the device may use simple LED indicator lights to provide the user with the appropriate feedback. For instance a small panel of LEDs can provide status indicators of on/off, positive tracking over the tissue or failure to track (indicating a need to reposition the device on the origin) as well as an indicator light to inform the user if the device is traveling over an area of tissue previously treated by the medical device. Similarly an audible tone can be used to alert the user to any problems with the device, or to alert the user to those times when the device is retracing paths it previously made. The visual representation is preferred as it would likely be the most helpful. The precise nature of the tracking ability allows the map to be relied on for accuracy in a medical procedure, as well as allowing for the repositioning of the device if needed.

The asymmetric flange 592 is shown being at the very bottom of the bottom section. When the device is placed against the skin of the patient at the outset of a procedure, the outline or footprint of the flange may be traced or marked appropriately on the skin. The markings create the reference position or origin and allow the device to be repositioned on the origin at any time. The flange is preferably asymmetric so the device can be position on the reference point in only one orientation. If the flange were a regular shape, the device could be positioned in the origin in any number of orientations that may not correspond with the proper initial orientation. When the medical device is an affecter for delivering radiant energy for therapeutic purposes, the orientation is critical to ensure the proper treatment of the tissue without over treating some areas and under treating others.

Figure 3C:
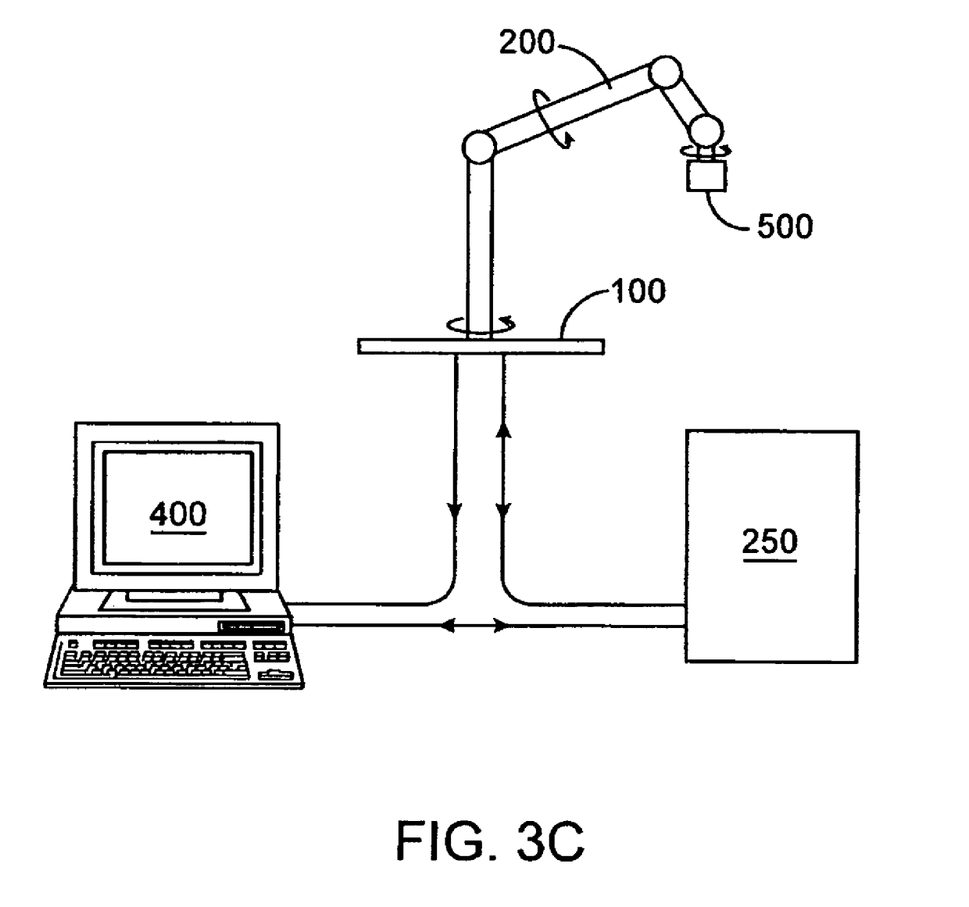
FIG. 3C illustrates the housing adapted to cooperate with a mechanical arm.

The position tracking device can be used as a stand alone instrument or as part of an ensemble. One possible combination is to use an articulated arm 200 to help support the weight of the device 550 (FIG. 3C). The articulated arm 200 may also include a position tracking system of its own that can be combined with that of the present invention. The combination would allow position information of the patient tissue, and information of movement based on an external coordinate system. Such a system is described in co-pending application Articulating Arm for Medical Procedure U.S. Application Ser. No. 10/751,344. Here the position tracking device 550 is operationally connected to a computer 400 and a therapy controller 250. Data from the on board processor 570 may be combined with data generated by the articulating arm 200 in the computer 400. Furthermore the data may be manipulated according to one or more programs designed to implement, or facilitate the implementation of a medical procedure. Thus the computer and any programs used with the computer during the medical procedures may help in the construction of a three dimensional map of the patient tissue, as well as real time tracking of the movement of the position tracking device 550 over the patient P. The position tracking can be used in conjunction with the three dimensional map to plot out both surface areas and tissue volumes that remain to be treated during a medical procedure. In addition the computer or medical device controller can act as an interrupt switch, turning the medical device 600 off when the position tracking device passes over tissue that has already been treated.

Methods of use with the present invention are now described.

Preliminary steps may be taken prior to using the position tracking device disclosed. Initially, the physician and/or patient must determine the surface area for treatment. Defining the surface involves the selection of a particular area the physician intends to treat according to the medical procedure to be performed. If a non-invasive procedure is to be performed, then the physician must define an area of skin that the device will be used on. If the procedure is to be an invasive one, then the physician or surgeon must ensure that there is sufficient space on the desired tissue for the device to be effectively usable on. The surface selection requires the surface be relatively smooth and free of irregular features that may cause the position tracking device to lose track of the tissue surface, or be an able to properly determine movement and distance information. Instances such as using the position tracking device over thick stands of body hair, or where there are abrupt corners or topographic irregularities, such as around the ear or nostril. Curved surfaces should not present a problem so long as the position tracking device is carefully moved in a way so the optical sensor maintains contact with the skin surface, even if the entire foot print of the position tracking device does not maintain contact.

Similarly the position tracking device may have varying shapes and sizes allowing it to be specifically adapted for different tissues. Larger housings can be used for non-invasive procedures while smaller housings can be used invasively for sitting on the surface of the kidneys, liver or other organs.

A secondary initial step involves preparing the surface. After the surface to be treated has been defined, it may be prepared. Preparation for use with the position tracking device requires the surface be relatively clean of particulate matter and smooth. Obviously when dealing with organic tissue an absolutely clean surface is impossible nor desirable, however the surface must be sufficiently clear of loose matter so as to not interfere with the position tracking device and the position tracking. Additional preparation of the tissue may be required to accommodate the medical procedure to be conducted.

Once the tissue area or volume has been selected and prepared, a procedure can begin.

Step 1. Placing the position tracking device on the patient. This step involves the proper placement of the device on the selected tissue area or volume to be treated. If the procedure is therapeutic, then it is beneficial to place the device on one part of the area and move the device to the opposite side of the area so as to minimize the potential for over exposing the tissue to the medical device. If the medical device is to be inserted, then it is preferable to offset the position tracking device so that it does not cover the area where the medical instrument is to be inserted. In this manner the position tracking instrument can be moved into position and provide for an origin position separate from the site of device insertion.

Step 2. Defining a reference position or origin. Once the position tracking device is set on the patient, it is necessary to establish a reference position to which the position tracking device can be accurately repositioned from. The asymmetric flange about the bottom section of the housing is used as a template for the physician or user to mark the patient. Alternatively a separate template that matches the asymmetric flange can be used prior to the placement of the device. Once the outline or reference position is marked, the separate template is removed and the housing can be set on the patient so the asymmetric flange matches the marking made.

The reference position need not be a complete outline of the asymmetric flange. Sufficient marks on the patient skin that provide with a clear indication of the original position of the device are sufficient. Alternatively the reference position may be delineated with a temporary tattoo, body sticker or other means of marking the patient's skin.

The optical sensors may also be sensitive to a particular color or ink type that allows the reference position to be made based on one or more markings for the optical sensors. In this case the user must have a readily identifiable indicator that the optical sensors have been properly positioned on the origin. Any combination or equivalent means may be used to those described herein.

The reference position does not have to be within the boundaries of the area to be treated. The reference position may be more conveniently located outside the boundary of the area to be treated, or may coincide with some natural reference on the patient body, such as a birth mark, scar, or even the patient's belly button.

Step 3. Calibrating the position tracking device to the reference position. In this step the user must actuate the on board processor or ancillary computer device so that the position tracking device will "zero" itself to the current position. This is necessary so the movement of the device from the origin can be tracked accurately. However the device must know when the origin has been determined.

Step 4. Treating the patient with a medical device enclosed within the position tracking device while tracking and recording all movement data. This is the operational step of actually treating the patient with the enclosed medical device. The position tracking device is moved over the surface of the patient body while the optical sensors keep track of movement. The medical device within the housing now transmits its own radiant energy into the patient. The on board processor may be operationally linked to the medical device through the medical device controller or an external computer system. In this manner the medical device may be switched on or off depending on the position of the device on the patient. Where the on board processor recognizes an area of the patient that has been previously treated, the medical device may turn off, or stop radiating energy. This prevents the area from being over treated. Alternatively the medical device controller or the external computer may perform the function of controlling the activity of the medical device, and coordinating that activity with the position of the housing according to the three dimensional/two dimensional map.

Sufficient contact between the housing and the patient must be maintained so that the optical sensors are able to properly determine their position. If at any time the optical sensors are unable to determine their position and orientation on the patient, then the optical sensors stop tracking and signal the on board processor that track of the patient has been lost. Once again this information is coordinated with the medical device controller and allows the medical device to cease radiating energy into the patient. The response to losing track is essentially instantaneous so there is no danger of stray emissions, or emissions that are not recorded by the data history.

The data history can also keep track of the progress of the radiant energy delivered into the patient. The medical device has a known affecter region that can be projected into the three dimensional map of the patient tissue. As the housing tracks over the patient, the medical device delivers either continuous or discrete bursts of radiant energy. Overlaying the distribution of the radiant energy can be performed by measuring the residence time of the housing over a specific position, and determining the amount of energy transmitted into the patient. The calculation takes advantage of knowing the affecter region of the medical device, the residence time over any particular position, and the three dimensional map of the tissue of interest.

The use of an imaging sensor such as an ultrasound device, is not necessary to create a map of the radiant energy deposited in the patient. So long as the affecter region of the medical instrument is known it can be projected downward from the two dimensional area map of the tissue being treated.

If the housing is removed from the surface of the patient for any reason, the physician need only reposition the housing on the reference position and begin the procedure again. The position tracking device must be recalibrated to the origin. However the data history will remain and the position tracking device will be able to effectively guide the physician to the untreated regions within the desired treatment region.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A position tracking device for recording movement of a medical device over a patient, said position tracking device comprising:
    a housing adapted to be moved relative to a patient, said housing having a top section and a bottom section, said bottom section having a primary transmissible window, and at least one secondary transmissible window;
    a movement sensor positioned to detect movement through said secondary transmissible window(s);
    an asymmetric patterned flange attached to said bottom section wherein said flange is positioned to lie over the patient's skin when said housing is moved relative to said patient; and
    a first medical device positioned within said housing to transmit energy through said primary transmissible window.

2. The device as described in claim 1, wherein said sensor comprises a processor operatively associated with one or more optical sensors.

3. The device as described in claim 2, wherein said processor relays movement data to a medical device controller.

4. The device of claim 2, wherein said processor relays said position and orientation data to a computer.

5. The system of claim 1, wherein the medical device comprises a therapeutic ultrasound transducer.

6. The system of claim 1, wherein the medical device comprises a laser.

7. The system of claim 1, wherein the medical device comprises a diagnostic ultrasound transducer.

8. The system of claim 1, wherein the medical device comprises a biopsy probe.

9. The system of claim 1, wherein the medical device comprises a microwave emitter.

10. The system of claim 1, wherein the medical device is a radiation source.

11. A position tracking device for recording movement of a medical device over a patient; said position tracking device comprising:
   a housing adapted to be moved relative to a patient, said housing having a top section and a bottom section, said bottom section having at least one transmissible window, and said housing having an aperture for slidably receiving a medical device, said aperture extending there through from said top section to said bottom section;
   a movement sensor positioned to detect movement through said transmissible windows;
   an asymmetric flange attached to said bottom section wherein said flange is positioned substantially near said patient when said housing is moved relative to said patient.

12. The device as described in claim 11, wherein said sensor comprises a processor operatively associated with one or more optical sensors.

13. The device as described in claim 12, wherein said processor relays position and orientation data to a medical device controller.

14. The device of claim 12, wherein said processor relays said position and orientation data to a computer.

15. The device as described in claim 11, wherein the medical device comprises a biopsy guide.

16. The device as described in claim 11, wherein the medical device comprises a catheter, guidewire or catheter insertion tool.

17. A position tracking device for recording movement of a medical device over a patient, said position tracking device comprising:
   a housing adapted to be moved relative to a patient, said housing having a top section and a bottom section, said bottom section having a primary transmissible window, at least one secondary transmissible window and an aperture for slidably receiving a medical instrument;
   a movement sensor positioned to detect movement through said secondary transmissible window(s);
   an asymmetric patterned flange attached to said bottom section wherein said flange is positioned substantially near said patient when said housing is moved relative to said patient; and
   a medical imaging device positioned within said housing to image patient tissue through said primary transmissible window.

18. A method of position tracking over human tissue comprising:
   (a) placing a position tracking device which produces movement data on a patient;
   (b) defining a reference position by marking the patient using an asymmetric flange of the position tracking device as a template;
   (c) calibrating said position tracking device to said reference position;
   (d) activating a medical device enclosed within said position tracking device while tracking and recording movement data from said position tracking device.

19. The method of claim 18, wherein the method further comprises:
   (e) communicating said movement data in real time to a medical device controller.

20. The method of claim 19, further comprising:
   (f) repositioning said position tracking device on said reference position after at least one movement data corresponding to image of said patient has been recorded.

* * * * *